United States Patent [19]

Fanshawe et al.

[11] 3,997,530

[45] Dec. 14, 1976

[54] SUBSTITUTED ENAMINOKETONES

[75] Inventors: William Joseph Fanshawe, Pearl River; Lantz Stephen Crawley, Spring Valley, both of N.Y.; Sidney Robert Safir, River Edge, N.J.; Gretchen Ellen Wiegand, deceased, late of Pearl River, N.Y.; by Earle Clifford Cooley, executor, Hingham, Mass.

[73] Assignee: American Cyanamid Company, Stamford, Conn.

[22] Filed: Mar. 25, 1976

[21] Appl. No.: 670,324

Related U.S. Application Data

[63] Continuation-in-part of Ser. No. 491,449, July 24, 1974, Pat. No. 3,957,805.

[52] U.S. Cl. .......................................... 260/240 R

[51] Int. Cl.$^2$ ............. C07D 213/38; C07D 213/50; C07D 241/00

[58] Field of Search ................................ 260/240 R

[56] References Cited

UNITED STATES PATENTS

| 3,530,120 | 9/1970 | Hirsch ..................... 260/240 R UX |
| 3,714,153 | 1/1973 | Martel ........................... 260/240 R |

*Primary Examiner*—Allen B. Curtis
*Attorney, Agent, or Firm*—Neal O. Willmann

[57] ABSTRACT

This application discloses novel substituted enaminoketones which possess analgesic and antipyretic activity in warm-blooded animals.

7 Claims, No Drawings

SUBSTITUTED ENAMINOKETONES

CROSS-REFERENCE TO RELATED APPLICATION

This application is a continuation-in-part of a copending U.S. Application, Ser. No. 491,449, filed July 24, 1974, now U.S. Pat. No. 3,957,805.

BRIEF SUMMARY OF THE INVENTION

Applicants invention discloses substituted enaminoketones of the following formulae:

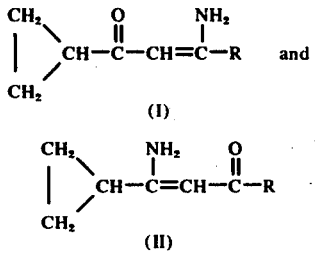

wherein R is selected from a group consisting of pyridyl, and pyrazinyl. The disclosed compounds possess analgesic and antipyretic activity in warm-blooded animals.

Pharmaceutically acceptable acid addition salts of substituted enaminoketones are considered to be within the purview of the present invention and can be prepared by direct neutralization of the free bases with the appropriate acid. These salts are those in which the anion does not contribute significant toxicity to the salt in the dosages thereof employed in accordance with the present invention. Examples of suitable salts are the acetate, propionate, butyrate, pamoate, mucate, citrate, maleate, tosylate, phosphate, nitrate, sulfate, hydrobromide, hydroiodide, hydrochloride, etc.

The enaminoketones of the present invention may be prepared by the reaction sequence shown below. In the first step, a ketone such as cyclopropylmethylketone is condensed with a pyridyl or pyrazinylcarboxylic acid ester in the presence of a base, such as sodium methoxide, in a non-polar solvent, such as benzene or toluene, at a temperature of 80° to 110° C. for a period of 1 to 24 hours to provide a 1-cyclopropyl-3-pyridyl (or pyrazinyl)-1,3-propanedione. The 1-cyclopropyl-3-pyridyl (or pyrazinyl)-1,3-propanedione is reacted with a hydroxylamine salt, such as the hydrochloride, in a polar solvent, such as ethanol, at a temperature of 25° to 80° C. for a period of 1 hour to 24 hours with the addition of a base, such as triethylamine to provide a mixture of isomeric monooximes. The mixture of monooximes is treated with an excess of an acidic reagent such as ethanolic hydrogen chloride or sulfuric acid, neat, or in the presence of a solvent such as methylene chloride to furnish a mixture of the isomeric cyclopropylisoxazolylpyridines or pyrazines. The mixture of isomeric isoxazoles can then be separated into the individual components by physical or chemical procedures as described in the Examples or carried through the reductive process without prior separation of the individual components.

The reductive process of the present invention may be accomplished by catalytic reduction using procedures well-known to those in the art. Catalytic reduction may be accomplished in a solvent for the starting compound in the presence of a carbonyl compound and a metal catalyst and hydrogen gas at pressures from atmospheric to super-atmospheric. Ordinarily, the reduction is conveniently carried out at hydrogen pressures of from about one to about four atmospheres. Temperatures do not appear to be critical in the catalytic hydrogation. Temperatures of from 0° C. to 50° C., and usually room temperature, are preferred since they generally give best results. The metal catalyst may be of the base metal type, such as nickel or copper chromite, or preferably, it may be of the noble metal type, such as finely divided platinum, palladium or rhodium. The noble metal catalysts are advantageously employed on a carrier such as finely divided alumina, activated charcoal, diatomaceous earth, etc., in which form they are commonly available, or they may be used without carriers. The hydrogenation is carried out until the desired amount of hydrogen gas is absorbed at which point the hydrogenation is stopped. The solvents selected for the catalytic reduction should be reaction-inert, that is, they should not be capable of reacting with the starting materials, product, or hydrogen under the conditions of the reaction. A variety of solvents may be used for this purpose and minimum laboratory experimentation will permit the selection of a suitable solvent for any starting compound. Generally, the catalytic reduction may be carried out in solvents such as water, lower alkanols, e.g. methanol, ethanol; lower alkoxy lower alkanols, e.g., 2-methoxyethanol, 2-ethoxyethanol; tetrahydrofuran, dioxane, dimethylformamide, etc.

The products are obtained from the reduction reaction mixtures by standard procedures. For example, the products may be isolated from the catalytic hydrogenation reaction mixtures, after filtration of the catalyst, by precipitation with a solvent such as ether or hexane or by concentration, usually under reduced pressure, or by a combination of these. Work-up of the chemical reduction reaction mixtures to obtain the desired products may also be accomplished by known procedures such as precipitation, concentration, solvent extraction, or combinations of these procedures. After isolation, the products may be purified by any of the generally known methods for purification. These include recrystallization from various solvents and mixed solvent systems, chromatographic techniques, and counter current distribution, all of which are usually employed for this purpose.

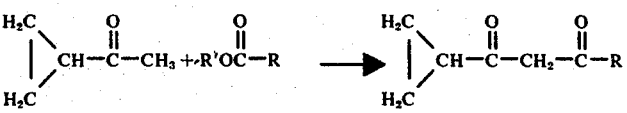

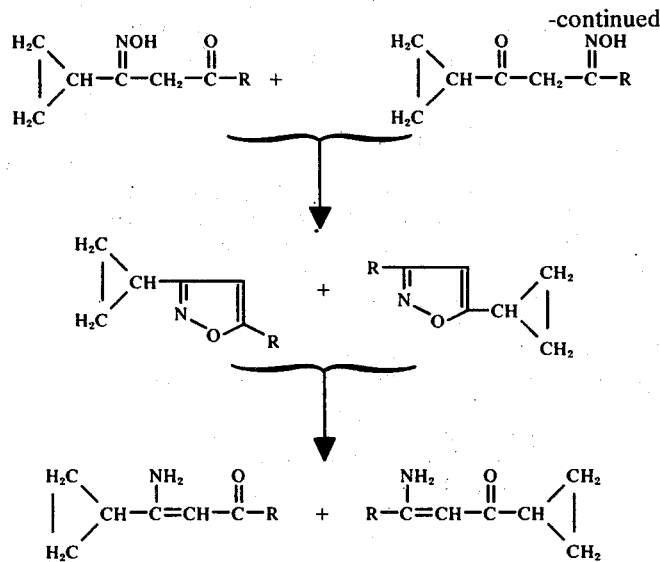

R is as hereinbefore defined, and R' is lower alkyl.

The substituted enaminoketones of the present invention are active analgesics when measured by the "writhing syndrome" test for analgesic activity as described by Siegmund, et al., Proc. Soc. Exp. Bio. and Med., 95, 729 (1957), with modifications. This method is based upon the reduction of the number of writhes following the intraperitoneal injection of one mg./kg. of body weight of phenyl-p-quinone in male Swiss albino mice weighing 18–25 gm. The syndrome is characterized by intermittent contractions of the abdomen, twisting and turning of the trunk, and extension of the hind legs beginning 3 to 5 minutes after injection of the phenyl-p-quinone. The test compounds are administered orally at the indicated dose to groups of 2 mice each, 30 minutes before injection of the phenyl-p-quinone. The total number of writhes exhibited by each group of mice is recorded for a 3 minute period commencing 15 minutes after injection of the phenyl-p-quinone. A compound is considered active if it reduces the total number of writhes in 2 test mice from a control value of approximately 30 pair to a value of 18 or less. Table I summarized the results of this test on representative compounds of this invention.

TABLE I

| Compound | Dose mg./kg. | No. of writhes per pair |
|---|---|---|
| 3-amino-3-cyclopropyl-1-(4-pyridyl)-2-propen-1-one | 100 | 9.4 |
| 1-amino-1-cyclopropyl-3-(2-pyrazinyl)-1-propen-3-one | 100 | 3.8 |

The compounds of this invention also exhibit analgesia in warm-blooded animals as evidenced by the Brewer's Yeast Pressure Pain Test. To determine analgesic activity, a modification of the method of Randall and Selitto [Arcy. int. Pharmacodyn., 111, 409 (1957)] is used. This test measures the pain threshold of rats whose paws are made sensitive to pressure by the injection of a 20% aqueous suspension (0.1 ml.) of brewers' yeast into the plantar surface of the left hind paw. Constantly increasing force (16 grams/second) is applied to the swollen paw using an Analgesy Meter, Ugo Basile. The pressure is cut off at 250 grams of force when there is no response (sudden struggle or vocalization). Control rats treated with the starch vehicle response to a pressure or force of about 30 grams. Pressure-pain thresholds are always recorded 2 hours after brewers' yeast. Analgesic agents are administered at the same time as the yeast, at a dose of 200 mg./kg. orally. Ratios of treated (T)/control (C) reaction thresholds are calculated as estimates of analgesic efficacy (degree of analgesia attainable). Potency is regarded as the dose necessary to produce a given level of analgesia (i.e. 100% elevation of pain threshold is T/C=2.0). Table I gives the results obtained with a representative compound.

TABLE II

| Compound | Ratio (Treated/Control) Measured at 2 Hours Following 200 mg./kg. Oral Dose |
|---|---|
| 3-Amino-3-cyclopropyl-1-(4-pyridyl)-2-propen-1-one | 1.45, 1.39 ($ED_{50}$ = 25 mg./kg.) |

The compounds of the present invention exhibit analgesic activity when measured by a modification of the method of D. C. Atkinson and A. Cowan, J. Pharm. Pharmac., 26, 727 (1974).

In this test male, albino Wistar strain rats from Royalhart farms, weighing 120–150 g. are deprived of food for about 20 hours. A 40% suspension of brewers' yeast in physiological saline is injected, at a concentration of 0.25 ml/rat into the plantar surface of the left hind paw of each rat. 3 hours later, at which time an inflammation of the injected paw has developed, a pre-drug assessment of walking gait is made for each rat according to the following scoring system:

0 = Normal gait in the presence of a severely inflammed paw. There is continuous use of the foot pad.

0.5 = As above with intermittent mild limping.

1.0 = Constant limping, but continuous use of the foot pad.

1.5 = Limping with occasional three-legged gait (paw kept off walking surface) or intermittent use of digits in combination with foot pad.

2.0 = Continuous three-legged gait and/or only the tips of the digits touch the walking surface. There is no use of foot pad.

More than 95% of the rats exhibit a gait score of 2 before given a test compound. Compounds, in a suitable vehicle, are administered orally by gavage in a volume of 0.5 ml./100 g. of body weight. One and/or two hours later a post-drug assessment of walking gait is made as described above. The criterion of an analgesic response for each rat is a 50% reversal of the abnormal gait score (post-drug) from the pre-drug score. An $ED_{50}$ represents a dose which produces a 50% reversal of the pre-dose score. The results of this test on representative compounds of the present invention appear in Table III.

TABLE III

| Compounds | $ED_{50}$ in mg./kg. |
| --- | --- |
| 3-Amino-3-cyclopropyl-1-(4-pyridyl)-2-propen-1-one | 40, 86, 66 |
| 3-Amino-3-cyclopropyl-1-(3-pyridyl)-2-propen-1-one | 27, 40, 26 |
| 1-Amino-1-cyclopropyl-3-(2-pyrazinyl)-1-propen-3-one | 71, 30 |

The compounds of this invention also show antipyretic activity by their ability to reduce a hyperthermic response in warm-blooded animals, e.g., rats, induced by the subcutaneous injection of a suspension of brewers' yeast. This is a modification of the method described by Teotino, et al., J. Med. Chem. 6, 248 (1963). A 40% suspension of brewer's yeast in distilled water is administered to groups of five to ten rats subcutaneously (1.0 ml./100 g. of body weight). Eighteen hours later, rectal temperatures are recorded and compounds, control vehicle (2% starch suspension) or aspirin is administered. Rectal temperatures are recorded 4 hours later and the results are compared with the starch treated controls and with aspirin, a reference antipyretic agent. For example, a representative compound, 3-amino-3-cyclopropyl-1-(4-pyridyl)-2-propen-1-one at a dose of 200 mg./kg. was effective in lowering the yeast-elevated body temperature of rats while not effecting the body temperature of normal rats. Aspirin is similarly effective in lowering yeast-elevated temperatures while not effecting the temperature of normal rats.

The active components of this invention can be used in compositions such as tablets; the principal active ingredient is mixed with conventional tabletting ingredients such as corn starch, lactose, surcose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or be delayed in release. A variety of materials can be used for such enteric layers or coatings, such materials including a number of polymeric acids or mixtures of polymeric acids with such materials as shellac, and shellac and cetyl alcohol, cellulose acetate and the like. A particularly advantageous enteric coating comprises a styrene maleic acid copolymer together with known materials contributing to the enteric properties of the coating.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The dosage may vary from 1 mg. to 70 mg. per kg. of warm-blooded animal per day, preferably in multiple doses. The daily dosage requirement may be from 50 mg. to 2000 mg. The specification for the novel dosage forms of this invention are indicated by characteristics of the active component and the particular therapeutic effect to be achieved or the limitations inherent in the art of compounding such as active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples or any of the foregoing and other forms as herein described.

DETAILED DESCRIPTION

The examples which follow describe the preparation of representative compounds of the present invention.

EXAMPLE 1

Preparation of 1-Cyclopropyl-3-(4-pyridyl)-1,3-propanedione

A mixture of 13.7 g. of methyl isonicotinate, 16.8 g. of cyclopropylmethyl ketone and 6 g. of sodium methoxide in 150 ml. of benzene is heated under reflux for 8 hours. The mixture is filtered and the collected solid is dissolved in water. The aqueous mixture is made weakly acidic with dilute hydrochloric acid and extracted with ether. The ethereal solution is dried over magnesium sulfate and concentrated under reduced pressure to give 1-cyclopropyl-3-(4-pyridyl)-1,3-propanedione as a mobile, yellow liquid, infra-red spectrum 6.15u ($CHCl_3$, $\beta$-diketone.

EXAMPLES 2 and 3

Preparation of 4-(5-Cyclopropyl-3-isoxazolyl)pyridine and 4-(3-cyclopropyl-5-isoxazolyl)pyridine To a stirred mixture of 47 g. of 1-cyclopropyl-3-(4-pyridyl)-1,3-propanedione, 26.7 g. of hydroxylamine hydrochloride, 290 ml. of ethanol, and 190 ml. of water is added slowly 26.7 g. of sodium carbonate. This solution is heated under reflux for 16 hours and the ethanol is evaporated under reduced pressure. The residue is diluted with 200 ml. of water and the aqueous mixture is extracted with chloroform. The chloroform solution is dried over magnesium sulfate and concentrated to a solid. Recrystallization from benzene-hexane gives cream-colored crystals, melting point 75°–80° C., which is a mixture of 4-(5-cyclopropyl-3-isoxazolyl)pyridine and 4-(3-cyclopropyl-5-isoxazolyl)pyridine. Treatment of this mixture by liquid-liquid partition chromatograph on a diatomaceous earth column with a heptane-acetonitrile-water system permits the separation of the components; namely 4-(5-cyclopropyl-3-isoxazolyl)pyridine as white crystals, melting point 81°–84° C., nmr spectrum δ6.84 (DMSO-$d_6$, s, 4-isoxazolyl H); and 4-(3-cyclopropyl-5-isoxazolyl)pyridine, as off-white crystals, melting point 102°–108° C., nmr spectrum δ7.02 (DMSO-$d_6$, s, 4-isoxazolyl H).

The 4-(5-cyclopropyl-3-isoxazolyl)pyridine forms a slightly water soluble citrate salt and 4-(3-cyclopropyl-5-isoxazolyl)pyridine forms a water soluble phosphate salt when treated with phosphoric acid.

EXAMPLES 4 and 5

Preparation of
3-Amino-3-cyclopropyl-1-(4-pyridyl)-2-propen-1-one
and 4-(5-cyclopropyl-3-isoxazolyl)pyridine A 1.0 g. sample of the mixture of 4-(5-cyclopropyl-3-isoxazolyl)pyridine and 4-(3-cyclopropyl-5-isoxazolyl)pyridine, obtained as described in Examples 2 and 3, is mixed with 0.125 g. of platinum oxide and 75 ml. of ethanol. This mixture is treated with hydrogen on a Parr apparatus at 40 psi for 2 hours at room temperature. The mixture is filtered and the filtrate concentrated to yield a solid. Recrystallization from ethyl acetate-petroleum ether (30°–60° C.) provides 3-amino-3-cyclopropyl-1-(4-pyridyl)-2-propen-1-one as white crystals, melting point 124°–125° C. The ethyl acetate petroleum ether (30°–60° C.) filtrate is concentrated to a solid which is recrystallized from aqueous ethanol to give 4-(5-cyclopropyl-3-isoxazolyl)pyridine as white crystals, melting point 78°–79.5° C., nmr spectrum δ6.85 (DMSO-$d_6$, s, 4-isoxazolyl H).

EXAMPLE 6

Preparation of
3-amino-1-cyclopropyl-3-(4-pyridyl)-2-propen-1-one

A solution of 3 g. of 4-(5-cyclopropyl-3-isoxazolyl)pyridine in 50 ml. of ethanol is treated with 0.5 g. of platinum oxide and the mixture is treated with hydrogen on a Parr apparatus at 44 psi for 5 hours at 25° C. The mixture is filtered and the filtrate is evaporated to dryness under reduced pressure to give a semi-solid residue which is recrystallized from ethyl acetate to give light tan crystals, melting point 159°–166° C.

EXAMPLE 7

Preparation of
1-cyclopropyl-3-(3-pyridyl)-1,3-propanedione

A mixture of 39 g. of ethyl nicotinate, 33 g. of cyclopropylmethyl ketone and 18 g. of sodium methoxide in 400 ml. of benzene is heated under refluxed for 6 hours. The mixture is diluted with 400 ml. of water and the benzene phase is separated. The aqueous phase is made weakly acidic with dilute hydrochloric acid and extracted with chloroform. The chloroform solution is dried over magnesium sulfate and concentrated under reduced pressure to give a solid. This solid is recrystallized from hexane to give colorless crystals, melting point 69°–70° C.

EXAMPLES 8 and 9

Preparation of
1-cyclopropyl-3-(3-pyridyl)-1,3-propanedione,
1-Oxime and
1-Cyclopropyl-3-(3-pyridyl)-1,3-propanedione,
3-Oxime A solution of 1.9 g. of 1-cyclopropyl-3-(3-pyridyl)-1,3-propanedione, 0.7 g. of hydroxylamine hydrochloride and 2.0 g. of triethylamine in 25 ml. of ethanol is heated under reflux for 5 hours. The solution is concentrated under reduced pressure and the residue is mixed with water. The aqueous mixture is extracted with chloroform, the chloroform solution dried over magnesium sulfate and concentrated under reduced pressure to give an oily solid. This solid is recrystallized from acetonitrile to give white crystals, melting point 114°–117° C.

EXAMPLES 10 and 11

Preparation of 3-(5-cyclopropyl-3-isoxazolyl)pyridine
and 3-(3-cyclopropyl-5-isoxazolyl)pyridine To 2.0 ml. of concentrated sulfuric acid is added slowly 0.33 g. of 1-cyclopropyl-3-(3-pyridyl)-1,3-propanedione, 1oxime and 1-cyclopropyl-3-(3-pyridyl)-1,3-propanedione, 3-oxime (Examples 8 and 9) with stirring at room temperature. The reaction is stirred at room temperature for 20 minutes and then poured onto cracked ice. The mixture is diluted with water, made basic with aqueous sodium hydroxide and extracted with chloroform. The chloroform solution is dried over magnesium sulfate and concentrated under reduced pressure to give a cream-colored solid. This solid is recrystallized from hexane to yield white crystals, melting point 73°–77° C., which is a mixture of 3-(5-cyclopropyl-3-isoxazolyl)pyridine and 3-(3-cyclopropyl-5-isoxazolyl)pyridine. Treatment of the mixture by liquid-liquid partition chromatography on a diatomaceous earth column with a heptane-acetonitrile system affords separation of the components; namely, 3-(5-cyclopropyl-3-isoxazolyl)pyridine as white crystals, melting point 74°–75° C., nmr spectrum δ6.82 (DMSO-$d_6$, s, 4-isoxazolyl H); 3-(3-cyclopropyl-5-isoxazolyl)pyridine as white crystals, melting point 73°75° C., nmr spectrum δ6.92 (DMSO-$d_6$, s, 4-isoxazolyl H).

The 3-(5-cyclopropyl-3-isoxazolyl)pyridine provides a slightly soluble acetate salt when treated with acetic acid and 3-(3-cyclopropyl-5-isoxazolyl)pyridine gives a water soluble sulfate salt following treatment with sulfuric acid.

EXAMPLES 12 and 13

Preparation of 3-(5-cyclopropyl-3-isoxazolyl)pyridine
and
3-amino-3-cyclopropyl-1-(3-pyridyl)-2-propen-1-one A 1.0 g. sample of the mixture of 3-(5-cyclopropyl-3-isoxazolyl)pyridine and 3-(3-cyclopropyl-5-isoxazolyl)pyridine, obtained as described in Examples 11 and 12, is mixed with 0.143 g. of platinum oxide and 75 ml. of ethanol. This mixture is treated with hydrogen on a Parr apparatus at 40 psi for 2 hours at room temperature. The mixture is filtered and the filtrate concentrated to yield a tacky, brown solid. The solid is dissolved in methanol and placed on preparative silica gel thin layer chromatographic plates and developed with 15% methanolbenzene. The least polar band is extracted to give 3-(5-cyclopropyl-3-isoxazolyl)pyridine as off-white crystals, melting point 70°–73° C. and the nmr spectrum δ6.82 (DMSO-d$_6$, s, 4-isoxazolyl H). The more polar fraction is extracted to give a viscous liquid. The 3-amino-3-cyclopropyl-1-(3-pyridyl)-2-propen-1-one is characterized as the diperchlorate salt, white crystals, melting point, 149°–154° C.

EXAMPLE 14

Preparation of
1-cyclopropyl-3-(2-pyridyl)-1,3-propanedione

A stirred mixture of 24 g. of ethyl picolinate, 18 g. of cyclopropylmethyl ketone and 11 g. of sodium methoxide in 250 ml. of benzene is heated under reflux for 6 hours. The mixture is diluted with 200 ml. of water and the water phase is removed. The aqueous solution is made weakly acidic with dilute hydrochloric acid. A solid precipitates and is collected by filtration. Recrystallization from cyclohexane provided colorless crystals, melting point 77°–78° C.

EXAMPLES 15 and 16

Preparation of
1-cyclopropyl-3-(2-pyridyl)-1,3-propanedione,
1-oxime and
1-Cyclopropyl-3-(2-pyridyl)-1,3-propanedione,
3-oxime A solution of 1.9 g. of 1-cyclopropyl-3-(2-pyridyl)-1,3-propanedione, 0.695 g. of hydroxylamine hydrochloride and 2.0 g. of triethylamine in 25 ml. of ethanol is heated under reflux for 5 hours. The reaction mixture is concentrated under reduced pressure and the residue is partially dissolved in 10 ml. of water. The aqueous mixture is extracted with chloroform, the chloroform solution is dried over magnesium sulfate and concentrated under reduced pressure to give the mixture of 1-cyclopropyl-3-(2-pyridyl)-1,3-propanedione, 1-oxime and 1-cyclopropyl-3-(2-pyridyl)-1,3-propanedione, 3-oxime as a viscous liquid. This liquid is used in Examples 21 and 22 without further purification.

EXAMPLES 17 and 18

Preparation of 2-(5-cyclopropyl-3-isoxazolyl)pyridine hydrochloride and
2-(3-cyclopropyl-5-isoxazolyl)pyridine hydrochloride A mixture of 0.354 g. of the mixture of 1-cyclopropyl-3-(2-pyridyl)-1,3-propanedione, 1-oxime and 1-cyclopropyl-3-(2-pyridyl)-1,3-propanedione, 3oxime (Examples 15 and 16) and 1.0 ml. of concentrated sulfuric acid is stirred for 20 minutes. This mixture is poured onto cracked ice and diluted with 50 ml. of water. The aqueous solution is made basic with 10N sodium hydroxide and extracted with chloroform. The chloroform solution is dried over magnesium sulfate and concentrated under reduced pressure to yield a yellow, mobile liquid. The liquid is dissolved in ethanol and acidified with ethanolic hydrogen chloride. Addition of ether precipitates a white solid, which is collected and recrystallized from acetonitrile to provide 2-(5-cyclopropyl-3-isoxazolyl)pyridine hydrochloride and 2-(3-cyclopropyl-5-isoxazolyl)pyridine hydrochloride as white crystals, melting point 159–162° C. Treatment of this mixture as the free base by liquid-liquid partition chromatography on a diatomaceous earth column with a heptane-acetonitrile system affords separation of the components; namely, 2-(5-cyclopropyl-3-isoxazolyl)pyridine, characterized as the hydrochloride, white crystals, melting point 132°–136° C., nmr spectrum δ6.79 (DMSO-d$_6$, s, 4-isoxazolyl H); and 2-(3-cyclopropyl-5-isoxazolyl)pyridine, characterized as the hydrochloride, melting point 164°–168° C., nmr spectrum δ6.88 DMSO-d$_6$, s, 4-isoxazolyl H).

EXAMPLES 19, 20 and 21

Preparation of 2-(5-cyclopropyl-3-isoxazolyl)pyridine hydrochloride,
3-amino-1-cyclopropyl-3-(2-pyridyl)-2-propen-1-one perchlorate and
3-amino-3-cyclopropyl-1-(2-pyridyl)-2-propen-1-one picrate An 8.3 g. sample of a mixture of 2-(5-cyclopropyl-3-isoxazolyl)pyridine hydrochloride and 2-(3-cyclopropyl-5-isoxazolyl)pyridine hydrochloride, obtained as described in Examples 21 and 22, is dissolved in aqueous sodium hydroxide and extracted with chloroform. The chloroform solution is dried over magnesium sulfate and concentrated to give a viscous liquid. The liquid is dissolved in 100 ml. of ethanol, 0.9 g. of platinum oxide added and the mixture treated with hydrogen on a Parr apparatus at 43 psi for 2.0 hours. The mixture is filtered and the filtrate concentrated to give a brown liquid. The liquid is dissolved in methanol and placed on silica gel preparative thin layer chromatographic plates and developed with 10% methanolbenzene. The least polar band in extracted to give a brown liquid. The liquid is dissolved in ethanol and acidified with ethanolic hydrogen chloride. Addition of ether precipitates a solid which is collected to provide 2-(5-cyclopropyl-3-isoxazolyl)pyridine hydrochloride as off-white crystals, nmr spectrum δ6.77 (DMSO-d$_6$, s, 4-isoxazolyl H). The most polar band is extracted to give a tacky solid. The solid is dissolved in ethanol and acidified with 70% perchloric acid. Addition of water precipitates a solid, which is collected and recrystallized from ethanol to afford 3-amino-1-cyclopropyl-3-(2-pyridyl)-2-propen-1-one perchlorate as yellow crystals, melting point 187°–188° C. The middle band is extracted to give a brown liquid, which is dissolved in ethanol and acidified with ethanolic picric acid. The crystals which form are collected and recrystallized from ethanol to give 3-amino-3-cyclopropyl-1-(2-pyridyl)-2-propen-1-one pictrate as light brown crystals, melting point 145°–150° C.

EXAMPLE 22

Preparation of
1-cyclopropyl-3-(2-pyrazinyl)-1,3-propanedione

A stirred mixture of 14.0 g. of methyl pyrazinoate, 16.8 g. of cyclopropylmethyl ketone, 6.0 g. of sodium methoxide and 200 ml. of benzene is heated under reflux for 5 hours. A 400 ml. volume of water is added to the mixture. The benzene phase is separated and the aqueous solution is made weakly acidic with dilute hydrochloric acid. A yellow solid precipitates, which is collected and recrystallized from hexane to give white crystals, m.p. 111°–112° C.

EXAMPLES 23 and 24

Preparation of
1-cyclopropyl-3-(2-pyrazinyl)-1,3-propanedione, 1-oxime and
1-cyclopropyl-3-(2-pyrazinyl)-1,3-propanedione, 3-oxime A mixture of 100 g. of 1-cyclopropyl-3-(2-pyrazinyl)-1,3-propanedione, 36 g. of hydroxylamine hydrochloride and 111.7 g. of triethylamine in 1000 ml. of ethanol is heated under reflux for 7 days. The ethanol is evaporated under reduced pressure and the residue is mixed with 500 ml. of water. The aqueous mixture is extracted with chloroform and the chloroform solution dried over magnesium sulfate. The chloroform solution is concentrated under reduced pressure to furnish a viscous, brown liquid. The liquid is used in Examples 30 and 31 without further purification.

EXAMPLES 25 and 26

Preparation of 2-(5-cyclopropyl-3-isoxazolyl)pyrazine and 2-(3-cyclopropyl-5-isoxazolyl)pyrazine A mixture of 1.0 g. of 1-cyclopropyl-3-(2-pyrazinyl)-1,3-propanedione, 1 and 3 oxime (Examples 23 and 24) and 5.0 ml. of concentrated sulfuric acid is stirred at room temperature for 25 minutes. The solution is poured onto cracked ice and diluted with 200 ml. of water. The mixture is made basic with 10N sodium hydroxide. The basic mixture is extracted with chloroform and the chloroform solution dried over magnesium sulfate. The chloroform solution is concentrated under reduced pressure to provide an off-white solid which is recrystallized from ethanol to give white crystals, m.p. 106°–109° C., which is a mixture of 2-(5-cyclopropyl-3-isoxazolyl)pyrazine and 2-(3-cyclopropyl-5-isoxazolyl)pyrazine. Separation of this mixture by liquid-liquid partition chromatograph on a diatomaceous earth column with a heptane-acetonitrile system provides 2-(5-cyclopropyl-3-isoxazolyl)pyrazine, as white crystals, m.p. 80°–81° C., nmr spectrum δ6.78 (DMSO-d$_6$, s, 4-isoxazolyl H) and of 2-(3-cyclopropyl-5-isoxazolyl)pyrazine as white crystals, m.p. 99°–100° C., nmr spectrum δ7.02 (DMSO-d$_6$, s, 4-isoxazolyl H).

EXAMPLES 27 and 28

Preparation of 2-(5-cyclopropyl-3-isoxazolyl)pyrazine and
1-amino-1-cyclopropyl-3-(2-pyrazinyl)-1-propen-3-one A 17 g. sample of the mixture of 2-(5-cyclopropyl-3-isoxazolyl)pyrazine and 2-(3-cyclopropyl-5-isoxazolyl)pyrasine, obtained as described in Examples 25 and 26, is mixed with 250 ml. of ethanol and 1.7 g. of platinum oxide. This mixture is treated with hydrogen on a Parr apparatus at 48 psi. for 2 hours at room temperature. The mixture is filtered and the filtrate concentrated under reduced pressure to give a brown tar. This tar is dissolved in methanol and placed on preparative silica gel thin layer chromatographic plates and developed with 10% methanol-benzene. The least polar band is extracted to give 2-(5-cyclopropyl-3-isoxazolyl)pyrazine as white crystals, melting point 80°–82° C., nmr spectrum δ6.77 (DMSO-d$_6$, s, 4-isoxazolyl H). The most polar band is extracted to yield the 1-amino-1-cyclopropyl-3-(2-pyrazinyl)-1-propen-3-one as a light brown solid which is recrystallized from acetonitrile to give dull yellow crystals, melting point 146°–150° C.

We claim:
1. Substituted enaminoketones of the formulae:

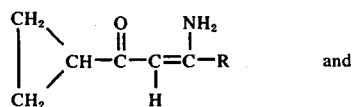

(I)

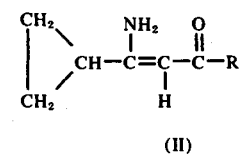

(II)

wherein R is selected from the group consisting of pyridyl and pyrazinyl.

2. The enaminoketone in accordance with claim 1, formula II, 3-amino-3-cyclopropyl-1-(4-pyridyl)-2-propen-1-one.

3. The enaminoketone in accordance with claim 1, formula II, 3-amino-3-cyclopropyl-1-(3-pyridyl)-2-propen-1-one.

4. The enaminoketone in accordance with claim 1, formula I, 3-amino-1-cyclopropyl-3-(2-pyridyl)-2-propen-1-one.

5. The enaminoketone in accordance with claim 1, formula II, 3-amino-3-cyclopropyl-1-(2-pyridyl)-2-propen-1-one.

6. The enaminoketone in accordance with claim 1, formula I, 1-amino-1-cyclopropyl-3-(2-pyrazinyl)-1-propen-3-one.

7. The enaminoketone in accordance with claim 1, formula I, 3-amino-1-cyclopropyl-3-(4-pyridyl)-2-propen-1-one.

* * * * *